United States Patent
Bianchi

(10) Patent No.: US 11,851,524 B2
(45) Date of Patent: Dec. 26, 2023

(54) BENZODITHIOPHENE CONJUGATED POLYMERS AND ORGANIC DEVICES CONTAINING THEM

(71) Applicant: ENI S.P.A., Rome (IT)

(72) Inventor: Gabriele Bianchi, Novara (IT)

(73) Assignee: ENI S.P.A., Rome (IT)

( * ) Notice: Subject to any disclaimer, the term of this patent is extended or adjusted under 35 U.S.C. 154(b) by 172 days.

(21) Appl. No.: 17/434,821

(22) PCT Filed: Mar. 6, 2020

(86) PCT No.: PCT/IB2020/051972
§ 371 (c)(1),
(2) Date: Aug. 30, 2021

(87) PCT Pub. No.: WO2020/178796
PCT Pub. Date: Sep. 10, 2020

(65) Prior Publication Data
US 2022/0145003 A1  May 12, 2022

(30) Foreign Application Priority Data

Mar. 6, 2019  (IT) .................. 102019000003241

(51) Int. Cl.
*C08G 61/12* (2006.01)
*H10K 85/10* (2023.01)

(52) U.S. Cl.
CPC ......... *C08G 61/126* (2013.01); *H10K 85/113* (2023.02); *C08G 2261/1426* (2013.01);
(Continued)

(58) Field of Classification Search
CPC .......... C08G 61/126; C08G 2261/1426; C08G 2261/3243; C08G 2261/344;
(Continued)

(56) References Cited

U.S. PATENT DOCUMENTS

2015/0333265 A1* 11/2015 Welker .................. C09B 69/102
549/4

FOREIGN PATENT DOCUMENTS

CN  104080780 A  10/2014
CN  104797624 A  7/2015

OTHER PUBLICATIONS

Cho et al; "Polymer solar cells fabricated with 4,8-bis(2-ethylhexyloxy) benzo [1,2-b:4,5-b] dithiophene and alkyl-substituted thiophene-3-carboxylate-containing conjugated polymers: effect of alkyl side-chain in thiophene-3-carboxylate monomer on the device performance"; Polymer; vol. 53; Jul. 5, 2012; pp. 3835-3841.
(Continued)

*Primary Examiner* — Shane Fang
(74) *Attorney, Agent, or Firm* — Ruggiero McAllister & McMahon LLC

(57) ABSTRACT

There is a benzodithiophene conjugated polymer of general formula (1):

(Continued)

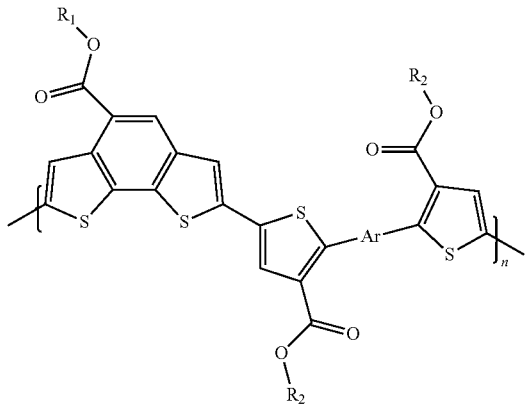

(I)

There are also photovoltaic devices having the polymer.
There are also organic devices having the polymer.

19 Claims, 3 Drawing Sheets

(52) U.S. Cl.
CPC .............. *C08G 2261/3243* (2013.01); *C08G 2261/344* (2013.01); *C08G 2261/91* (2013.01); *C08G 2261/92* (2013.01); *C08G 2261/95* (2013.01)

(58) Field of Classification Search
CPC ............ C08G 2261/91; C08G 2261/92; C08G 2261/95; H10K 85/113
See application file for complete search history.

(56) References Cited

OTHER PUBLICATIONS

International Search Report dated Apr. 28, 2020 for PCT Appl. No. PCT/IB2020/051972.
Written Opinion Report dated Apr. 28, 2020 for PCT Appl. No. PCT/IB2020/051972.
Chinese Office Action dated Apr. 1, 2023 from corresponding Chinese Patent Application No. 2023040100034000, 7 pages.
Nitti et al.; Scalable Synthesis of Naphthothiophene and Benzodithiophene Scaffolds as π-Conjugated Synthons for Organic Materials, Synthesis 2019, 51, pp. 677-682.

* cited by examiner

BENZODITHIOPHENE CONJUGATED POLYMERS AND ORGANIC DEVICES CONTAINING THEM

CROSS-REFERENCE TO RELATED APPLICATIONS

This patent application is a national stage application claiming priority from PCT Application No. PCT/IB2020/051972, which claims priority from Italian Patent Application No. 102019000003241 filed on Mar. 6, 2019, the entire disclosure of which is incorporated herein by reference.

FIELD OF THE DISCLOSURE

The present disclosure relates to a benzodithiophene conjugated polymer.

More particularly, the present disclosure relates to a benzodithiophene conjugated polymer comprising thiophenic groups substituted with ester groups, and electron-acceptor groups or electron-donor groups.

Accordingly, the present disclosure also relates to organic devices containing said benzodithiophene conjugated polymer.

DESCRIPTION OF THE RELATED ART

Photovoltaic devices (or solar devices) are devices capable of converting the energy of a light radiation into electricity. Currently, most photovoltaic devices (or solar devices) usable for practical applications, exploit the chemical-physical properties of photoactive materials of the inorganic type, in particular high purity crystalline silicon. Due to the high production costs of silicon, however, scientific research has long been directing its efforts towards the development of alternative organic-type materials having a conjugated, oligomeric or polymeric structure, in order to obtain organic photovoltaic devices (or solar devices) such as, for example, organic photovoltaic cells (or solar cells). In fact, unlike high purity crystalline silicon, said organic-type materials are characterized by a relative ease of synthesis, a low production cost, a reduced weight of the relative organic photovoltaic devices (or solar devices), as well as allowing said organic-type materials to be recycled at the end of the life cycle of the organic photovoltaic device (or solar device) in which they are used.

The above mentioned advantages make the use of said organic-type materials energetically and economically attractive despite any lower efficiencies (η) of the organic photovoltaic devices (or solar devices) thus obtained compared to inorganic photovoltaic devices (or solar devices).

The operation of the organic photovoltaic devices (or solar devices) such as, for example, organic photovoltaic cells (or solar cells), is based on the combined use of an electron-acceptor compound and an electron-donor compound. In the state of the art, the electron-acceptor compounds most commonly used in organic photovoltaic devices (or solar devices) are fullerene derivatives, in particular PC61BM (6,6-phenyl-$C_{61}$-methylester butyric) or PC71BM (6,6-phenyl-$C_{71}$-methylbutyric ester), which led to the greatest efficiencies (η) when mixed with electron-donor compounds selected from π-conjugated polymers such as, for example, polythiophenes (η>5%), polycarbazoles (η>6%), derivatives of poly(thienothiophene)benzodithiophene (PTB) (η>8%).

It is known that the elementary process of converting light into electric current in an organic photovoltaic cell (or solar cell) takes place through the following stages:

1. absorption of a photon by the electron-donor compound with the formation of an exciton, i.e. pair of "electron-electronic gap (or hole)" charge carriers
2. diffusion of the exciton in a region of the electron-donor compound up to the interface with the electron-acceptor compound;
3. dissociation of the exciton in the two charge carriers: electron (−) in the accepting phase (i.e. in the electron-acceptor compound) and electronic gap [(or hole) (+)] in the donor phase (i.e. in the electron-donor compound);
4. transport of the charges thus formed to the cathode (electron through the electron-acceptor compound) and to the anode [electronic gap (or hole) through the electron-donor compound], with generation of an electric current in the circuit of the organic photovoltaic cell (or solar cell).

The photoabsorption process with formation of the exciton and subsequent transfer of the electron to the electron-acceptor compound involves the excitation of an electron from the HOMO ("Highest Occupied Molecular Orbital") to the LUMO ("Lowest Unoccupied Molecular Orbital") of the electron-donor compound and, subsequently, the passage therefrom to the LUMO of the electron-acceptor compound.

Since the efficiency of an organic photovoltaic cell (or solar cell) depends on the number of free electrons that are generated by dissociation of excitons which is in turn directly correlated to the number of absorbed photons, one of the structural characteristics of the electron-donor compounds that mostly affects this efficiency is the difference in energy existing between the HOMO and LUMO orbitals of the electron-donor compound, that is the so-called "band-gap". In particular, the maximum value of the wavelength at which the electron-donor compound is able to effectively harvest and convert photons into electricity, i.e. the so-called "light harvesting" or "photon harvesting" process, depends on this difference. In order to obtain acceptable electric currents, the "band gap", that is the difference in energy between HOMO and LUMO of the electron-donor compound, on the one hand must not be too high so as to allow the absorption of the largest number of photons and on the other hand it must not be too low because it could decrease the voltage to the electrodes of the device.

In the simplest way of operating, organic photovoltaic cells (or solar cells) are manufactured by introducing between two electrodes, usually consisting of indium-tin oxide (ITO) (anode) and aluminum (Al) (cathode), a thin layer (about 100 nanometers) of a mixture of the electron-acceptor compound and the electron-donor compound (an architecture known as "bulk heterojunction"). Generally, in order to make a layer of this type, a solution of the two compounds is prepared and, subsequently, a photoactive film is created on the anode [indium-tin oxide (ITO)] starting from said solution, using suitable deposition techniques such as, for example, "spin-coating", "spray-coating", "ink-jet printing", and the like. Finally, the counter electrode [i.e. the aluminum cathode (Al)] is deposited on the dried film. Optionally, other additional layers can be introduced between the electrodes and the photoactive film, which layers are capable of performing specific functions of an electrical, optical, or mechanical nature.

Generally, in order to facilitate the achievement of the anode [indium-tin oxide (ITO)] by the electronic gaps (or holes) and at the same time to block the transport of electrons, thus improving the harvest of charges by the electrode and inhibiting the recombination phenomena, before creating the photoactive film starting from the mixture of the electron-acceptor compound and the electron-donor compound as reported above, a film is deposited starting from an aqueous suspension of PEDOT:PSS [poly (3,4-ethylene dioxythiophene)polystyrene sulfonate], using suitable deposition techniques such as, for example, "spin-coating", "spray-coating", "ink-jet printing", and the like.

Polymeric photovoltaic cells (or solar cells) with inverted structure are also known. Generally, the polymeric photovoltaic cells (or solar cells) with inverted structure reported in the literature comprise the following layers: (i) a support of transparent material; (ii) an indium-tin oxide (ITO) cathode; (iii) a cathodic buffer layer which has the function of electron carrier and electronic gaps (or holes) barrier generally comprising zinc oxide; (iv) an active layer comprising an electron-donor compound and an electron-acceptor compound; (v) an anodic buffer layer which has the function of electronic gaps (or holes) carrier and electron barrier comprising a hole-transporting material, generally selected from molybdenum oxide, tungsten oxide, vanadium oxide, (vi) generally, a silver (Ag), gold (Au) or aluminum (Al) anode.

The electron-donor compound most commonly used in the realization of organic photovoltaic cells (or solar cells) is the regioregular poly(3-hexylthiophene) (P3HT). This polymer has optimal electronic and optical characteristics (good values of the HOMO and LUMO orbitals, good molar absorption coefficient), good solubility in the solvents that are used to manufacture photovoltaic cells (or solar cells) and a moderate mobility of the electronic gaps.

Other examples of polymers that can be advantageously used as electron-donor compounds are: the PCDTBT polymer {poly [N-9''-heptadecanil-2,7-carbazole-alt-5,5-(4',7'-di-2-thienyl-2',1',3'-benzothiadiazole]}, the PCPDTBT polymer {poly[2,6-(4,4-bis-(2-ethylhexyl)-4H-cyclopenta[2,1-b;3,4-b']dithiophene)-alt-4,7(2,1,3-benzothiadiazole)]}.

Electron-donor compounds containing benzodythiophenic units are also known which have a structure similar to poly(3-hexylthiophene) (P3HT) in which, however, the thiophenic units are planarized by benzene rings. This feature, in addition to reducing the oxidation potential of said electron-donor compounds, improves their stability in the air and ensures their rapid packaging and, consequently, a high molecular order, during the realization of the photoactive film: this results in excellent charge transport properties [electrons or electronic gaps (holes)]. Consequently, the use of electron-donor compounds containing benzodithiophenic units can allow the realization of photovoltaic devices with better performances.

For example, electron-donor compounds containing benzodythiophenic units are described by Huo L. and others in the article: "Synthesis of a polythieno[3,4-b]thiophene derivative with a low-lying HOMO level and its application in polymer solar cells", "*Chemical Communication*" (2011). Vol. 47, p. 8850-8852. Said article describes the preparation of a polythieno[3,4-b]thiophene derivative by copolymerization between a planar benzodithiophene having a low HOMO value with a thieno[3,4-b]thiophenic unit.

Benzodithiophene and/or isomers thereof [e.g., benzo[1,2-b:4,5-b']dithiophene or (BDT) and benzo[2,1-b:3,4-b']dithiophene or (BDP)], are known to be compounds of significant interest whose synthesis has been the subject of numerous researches.

Generally, the electron-donor compounds used in high efficiency photovoltaic cells are almost exclusively represented by polymers in which an electron-rich unit alternates with an electron-poor unit. Further details relating to said polymers can be found, for example, in the following articles: Yu L. and others, "How to design low bandgap polymers for highly efficient organic solar cells", "*Materials Today*" (2014), Vol. 17, No. 1, p. 11-15; You W. and others: "Structure-Property Optimizations in Donor Polymers via Electronics, Substituents, and Side Chains Toward High Efficiency Solar Cells", "*Macromolecular Rapid Communications*" (2012), Vol. 33, p. 1162-1177; Havinga E. E. and others: "A new class of small band gap organic polymer conductors", "*Polymer Bulletin*" (1992), Vol. 29, p. 119-126.

However, said electron-donor polymers are not always optimal. In fact, since the flow of photons of the solar radiation that reaches the surface of the earth is maximum for energy values around 1.8 eV (corresponding to radiations having a wavelength of about 700 nm), due to the high "band-gap" values (generally greater than 2 eV-3 eV) that characterize many of the aforementioned electron-donor polymers, the so-called "light harvesting" or "photon harvesting" process is not very efficient and only a part of the total solar radiation is converted into electricity.

In order to improve the yield of the so-called "light harvesting" or "photon harvesting" process and, consequently, the efficiency of organic photovoltaic (or solar) devices, it is therefore essential to identify new electron-donor polymers capable of capturing and converting the wavelengths of solar radiation having lower energy, i.e. electron-donor polymers characterized by lower "band-gap" values than those of the polymers typically used as electron-donors.

To this end, efforts have been made in the art to identify electron-donor polymers having a low band gap value (i.e. a "band gap" value of approximately 2 eV-2.15 eV).

For example, one of the most commonly used strategies for obtaining electron-donor polymers having a low "band-gap" value is the synthesis of alternate conjugated polymers comprising electron-rich units (donor) and electron-poor units (acceptor). A synthesis of this type is described, for example by Chen J. and others in the article "Development of Novel Conjugated Donor Polymers for High-Efficiency Bulk-Heterojunction Photovoltaic Devices", "Account of Chemical Research" (2009), Vol. 42(11), p. 1709-1718.

The American patent application US 2015/0333265 describes polymers comprising functionalized benzodythiophenic units which are said to be advantageously used as organic semiconductors in electronic organic devices, in particular in organic photovoltaic devices or in photodiodes, or in devices containing a diode or in "Organic Field Effect Transistors"—(OFETs).

Cho M. J. and others, in "*Polymer*" (2012), Vol. 53, p. 3835-3841, describe polymeric solar cells containing 4,8-bis(2-ethylhexyloxy)benzo[1,2-b:4,5-b']dithiophene and conjugated polymers containing thiophenes substituted with ester groups. The aforesaid solar cells are said to decrease their performance, in particular in terms of energy conversion efficiency ($PCE_{av}$), as the chain length of the ester groups present on the thiophenes increases.

Since both organic photovoltaic (or solar devices), and "Organic Thin Film Transistors" (OTFTs), or "Organic Field Effect Transistors" (OFETs), or the "Organic Light-Emitting Diodes" (OLEDs), are still of great interest, the study of new conjugated electron-donor polymers that can be advantageously used therein, is still of great interest.

The Applicant has therefore addressed the problem of finding conjugated electron-donor polymers having a low "band gap" value (i.e. a "band gap" value of approximately 2 eV-2.15 eV), which can be used in the construction of organic devices, in particular, both in the construction of photovoltaic devices (or solar devices) such as, for example, photovoltaic cells (or solar cells), photovoltaic modules (or solar modules), either on a rigid support, or on a flexible support, and in the construction of "Organic Thin Film Transistors" (OTFTs), "Organic Field Effect Transistors" (OFETs), "Organic Light-Emitting Diodes" (OLEDs).

SUMMARY OF THE DISCLOSURE

The Applicant has now found new electron-donor conjugated polymers, in particular benzodithiophene conjugated polymers comprising thiophenic groups substituted with ester groups, and electron-acceptor groups or electron-donor groups, having the specific general formula (I) given below. Said benzodithiophene conjugated polymers have a low "band gap" value (i.e. a "band gap" value of approximately 2 eV-2.15 eV) and can be advantageously used in the construction of organic devices, in particular, both in the construction of photovoltaic devices (or solar devices) such as, for example, photovoltaic cells (or solar cells), photovoltaic modules (or solar modules), either on a rigid support, or on a flexible support, and in the construction of "Organic Thin Film Transistors (OTFTs), "Organic Field Effect Transistors" (OFETs), "Organic Light-Emitting Diodes" (OLEDs).

Therefore, the object of the present disclosure is a benzodithiophene conjugated polymer of general formula (I):

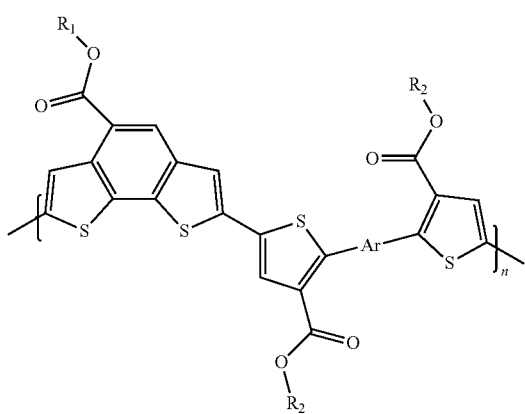

(I)

wherein:
R$_1$ and R$_2$, mutually identical or different, are selected from linear or branched, saturated or unsaturated, preferably C$_2$-C$_{20}$, C$_1$-C$_{30}$ alkyl groups; optionally substituted cycloalkyl groups; optionally substituted aryl groups; optionally substituted heteroarylic groups; linear or branched, preferably C$_2$-C$_{20}$, C$_1$-C$_{30}$ alkoxy groups; thiol groups —S—R$_3$ wherein R$_3$ is selected from linear or branched, saturated or unsaturated, preferably C$_2$-C$_{20}$, C$_1$-C$_{30}$ alkyl groups; polyethylenoxy groups R$_4$—O—[CH$_2$—CH$_2$—O]$_m$— wherein R$_4$ is selected from linear or branched, saturated or unsaturated, preferably C$_2$-C$_{20}$, C$_1$-C$_{30}$ alkyl groups and n is an integer ranging from 1 to 4; —R$_5$—OR$_6$ groups wherein R$_5$ is selected from linear or branched, preferably C$_2$-C$_{20}$, C$_1$-C$_{30}$ alkylene groups, and R$_6$ represents a hydrogen atom, or it is selected from linear or branched, saturated or unsaturated, preferably C$_2$-C$_{20}$, C$_1$-C$_{30}$ alkyl groups; —COR$_7$ groups wherein R$_7$ is selected from linear or branched, saturated or unsaturated, preferably C$_2$-C$_{20}$, C$_1$-C$_{30}$ alkyl groups; —COOR$_8$ groups wherein R$_8$ is selected from linear or branched, saturated or unsaturated, preferably C$_2$-C$_{20}$, C$_1$-C$_{30}$ alkyl groups; polyethylenoxy groups R$_9$—[—OCH$_2$—CH$_2$—]$_p$— wherein R$_9$ is selected from linear or branched, saturated or unsaturated, preferably C$_2$-C$_{20}$, C$_1$-C$_{30}$ alkyl groups, and p is an integer ranging from 1 to 4; R$_{10}$-T groups wherein R$_{10}$ is selected from linear or branched, saturated or unsaturated, preferably C$_2$-C$_{20}$, C$_1$-C$_{30}$ alkyl groups and T represents a polyalcohol group —OCH$_2$—CHOH—CH$_2$OH, or an amino group —N(CH$_3$)$_2$, or a carboxylic group —CO$_2$H, or a —CHO group, or a cyano group (—CN);
Ar represents an electron-acceptor group or an electron-donor group;
n is an integer ranging from 10 to 500, preferably ranging from 20 to 300.

Said benzodithiophene conjugated polymer can be advantageously used in the construction of organic devices, in particular photovoltaic devices (or solar devices) such as, for example, photovoltaic cells (or solar cells), photovoltaic modules (or solar modules), either on a rigid support, or on a flexible support. Furthermore, said benzodithiophene conjugated polymer can be advantageously used in the construction of organic devices such as, for example, "Organic Thin Film Transistors" (OTFTs), "Organic Field Effect Transistors" (OFETs), "Organic Light-Emitting Diodes" (OLEDs).

DETAILED DESCRIPTION OF THE DISCLOSURE

Figure 1:
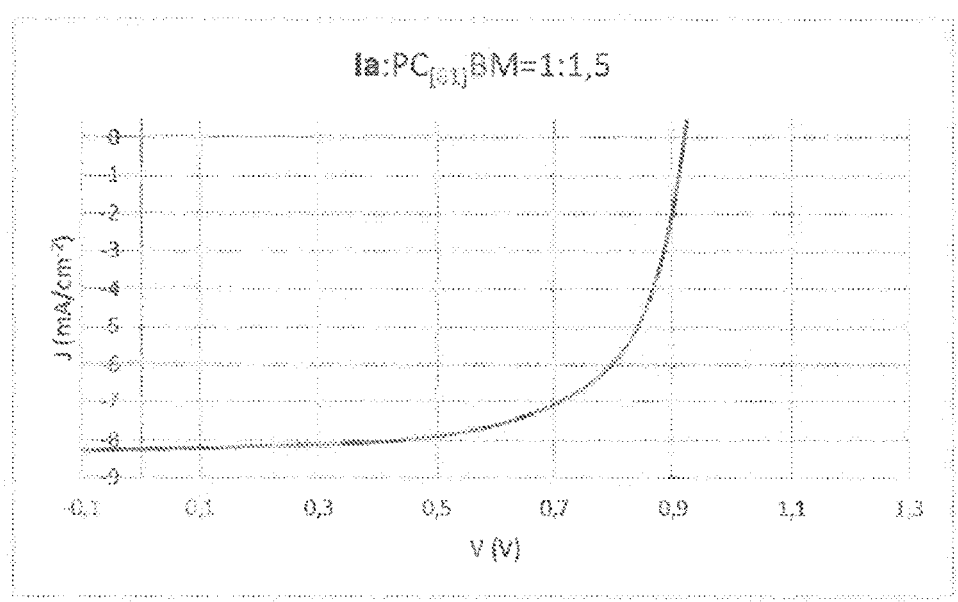
FIG. 1 is a plot of the current-voltage curve (I-V) obtained wherein the abscissa depicts the voltage in volts (V) and the ordinate depicts the short circuit current density (Jsc) in milliamps/cm$^2$ (mA/cm$^2$).

In accordance with a preferred embodiment of the present disclosure, in said general formula (I), Ar can be selected, for example, from the groups shown in Table 1.

TABLE 1

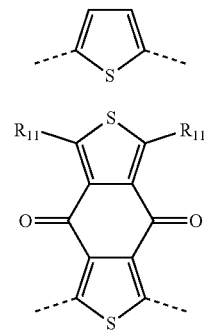

TABLE 1-continued
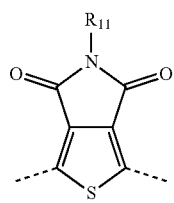
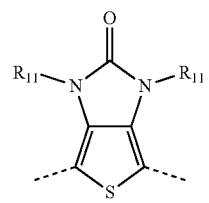
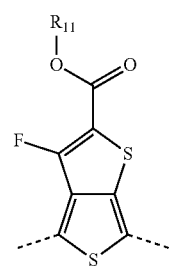
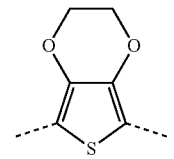
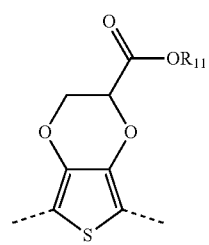
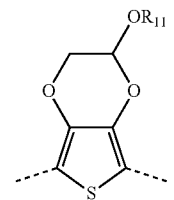
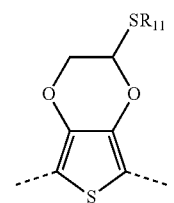
TABLE 1-continued
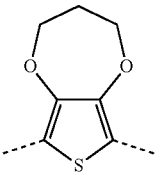
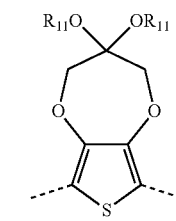
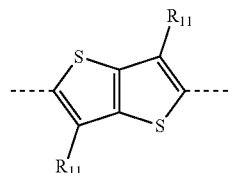
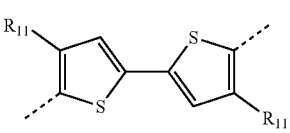
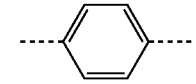
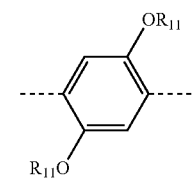
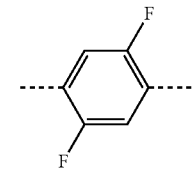
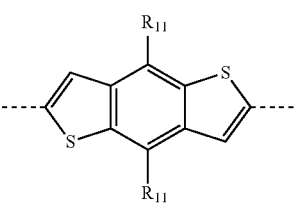
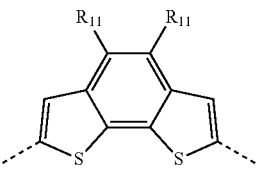

TABLE 1-continued

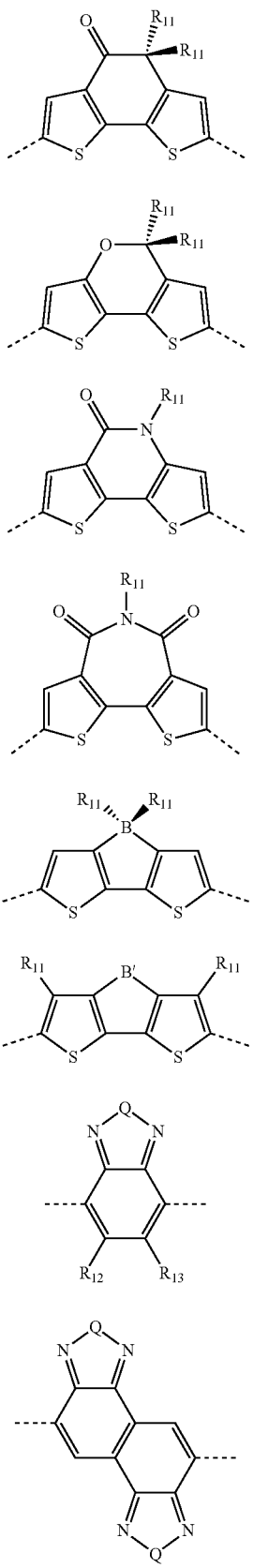

TABLE 1-continued

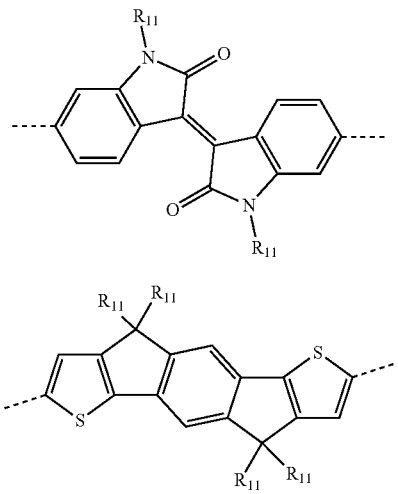

wherein:
B represents a sulfur atom, an oxygen atom, a selenium atom; or it represents a N—$R_{14}$ group wherein $R_{14}$ represents a hydrogen atom, or it is selected from linear or branched, saturated or unsaturated, preferably $C_6$-$C_{26}$, $C_1$-$C_{30}$ alkyl groups;

B' represents a carbon atom, a silicon atom, a germanium atom;

Q represents a nitrogen atom, a sulfur atom, an oxygen atom, a selenium atom; or it represents a C—$R_{14}$ group wherein $R_{14}$ has the same meanings given above;

$R_{11}$, mutually identical or different, are selected from linear or branched, saturated or unsaturated, preferably $C_2$-$C_{20}$, $C_1$-$C_{30}$ alkyl groups; optionally substituted cycloalkyl groups; optionally substituted aryl groups; optionally substituted heteroarylic groups; linear or branched, saturated or unsaturated, preferably $C_2$-$C_{20}$, $C_1$-$C_{30}$ alkoxy groups; polyethylenoxy groups $R_{15}$—[—$OCH_2$—$CH_2$—]$_q$— wherein $R_{15}$ is selected from linear or branched, saturated or unsaturated, preferably $C_2$-$C_{20}$, $C_1$-$C_{30}$ alkyl groups, and q is an integer ranging from 1 to 4; —$R_{16}$—$OR_{17}$ groups wherein $R_{16}$ is selected from linear or branched, saturated or unsaturated, preferably $C_2$-$C_{20}$, $C_1$-$C_{30}$ alkylene groups and $R_{17}$ represents a hydrogen atom, or it is selected from linear or branched, saturated or unsaturated, preferably $C_2$-$C_{20}$, $C_1$-$C_{30}$ alkyl groups; —$COR_{17}$ groups wherein $R_{17}$ has the same meanings given above; —$COOR_{17}$ groups wherein $R_{17}$ has the same meanings given above; or they represent a —CHO group, or a cyano group (—CN);

$R_{12}$ and $R_{13}$, mutually identical or different, represent a hydrogen atom, a fluorine atom; or they are selected from linear or branched, saturated or unsaturated, preferably $C_2$-$C_{20}$, $C_1$-$C_{30}$ alkyl groups; optionally substituted cycloalkyl groups; optionally substituted aryl groups; linear or branched, preferably $C_2$-$C_{20}$, $C_1$-$C_{30}$ alkoxy groups; polyethylenoxy groups $R_{15}$—[—$OCH_2$—$CH_2$—]$_q$— wherein $R_{15}$ has the same meanings given above and q is an integer ranging from 1 to 4; —$R_{16}$—$OR_{17}$ groups wherein $R_{16}$ and $R_{17}$ have the same meanings given above; —$COR_{17}$ groups wherein $R_{17}$ has the same meanings given above; —$COOR_{17}$ groups wherein $R_{17}$ has the same meanings given above; or they represent a —CHO group, or a cyano group (—CN);

$R_{12}$ and $R_{13}$, can be optionally linked to each other so as to form, together with the carbon atoms to which they are bonded, a saturated, unsaturated, or aromatic, cycle or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium.

In accordance with a preferred embodiment of the present disclosure, in said general formula (I):

$R_1$ is selected from linear or branched, preferably $C_2$-$C_{20}$, $C_1$-$C_{30}$ alkyl groups; preferably 2-octyl-dodecyl group;

$R_2$, mutually identical or different, preferably mutually identical, are selected from linear or branched, preferably $C_2$-$C_{20}$, $C_1$-$C_{30}$ alkyl groups; preferably n-octyl group;

Ar represents an electron-donor group, preferably thiophene;

n is an integer ranging from 20 to 300.

For the purposes of the present description and the following claims, the definitions of the numerical intervals always comprise the extreme values unless otherwise specified.

For the purpose of the description and the following claims, the term "comprising" also includes also the terms "which essentially consists of" or "which consists of".

For the purpose of the present description and the following claims, the term "$C_1$-$C_{30}$ alkyl groups" means alkyl groups having from 1 to 30 linear or branched, saturated or unsaturated, carbon atoms. Specific examples of $C_1$-$C_{30}$ alkyl groups are: methyl, ethyl, n-propyl, iso-propyl, n-butyl, iso-butyl, tert-butyl, pentyl, ethyl-hexyl, hexyl, heptyl, n-octyl, nonyl, decyl, dodecyl, 2-octyl-dodecyl.

For the purpose of the present description and the following claims, the term "cycloalkyl groups" means cycloalkyl groups having from 3 to 30 carbon atoms. Said cycloalkyl groups can optionally be substituted with one or more groups, mutually identical or different, selected from: halogen atoms such as, for example, fluorine, chlorine, bromine, preferably fluorine; hydroxyl groups; $C_1$-$C_{12}$ alkyl groups; $C_1$-$C_{12}$ alkoxy groups; $C_1$-$C_{12}$ thioalkoxy groups; $C_3$-$C_{24}$ tri-alkylsilyl groups; polyethylene oxyl groups; cyano groups; amino groups; $C_1$-$C_{12}$ mono- or di-alkylamine groups; nitro groups. Specific examples of cycloalkyl groups are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl, decalin, abietyl.

For the purpose of the present description and the following claims, the term "aryl groups" means aromatic carbocyclic groups having from 6 to 60 carbon atoms. Said aryl groups can optionally be substituted with one or more groups, mutually identical or different, selected from: halogen atoms such as, for example, fluorine, chlorine, bromine, preferably fluorine; hydroxyl groups; $C_1$-$C_{12}$ alkyl groups; $C_1$-$C_{12}$ alkoxy groups; $C_1$-$C_{12}$ thioalkoxy groups; $C_3$-$C_{24}$ tri-alkylsilyl groups; polyethylene oxyl groups; cyano groups; amino groups; $C_1$-$C_{12}$ mono- or di-alkylamine groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthene, phenanthenene, anthracene.

For the purpose of the present description and the following claims, the term "heteroaryl groups" means heterocyclic aromatic, penta- or hexa-atomic groups, also benzo-condensed or heterobicyclic, containing from 4 to 60 carbon atoms and from 1 to 4 heteroatoms selected from nitrogen, oxygen, sulfur, silicon, selenium, phosphorus. Said heteroaryl group can optionally be substituted with one or more groups, mutually identical or different, selected from: halogen atoms such as, for example, fluorine, chlorine, bromine, preferably fluorine; hydroxyl groups; $C_1$-$C_{12}$ alkyl groups; $C_1$-$C_{12}$ alkoxy groups; $C_1$-$C_{12}$ thioalkoxy groups; $C_3$-$C_{24}$ tri-alkylsilyl groups; polyethylene oxyl groups; cyano groups; amino groups; $C_1$-$C_{12}$ mono- or di-alkylamine groups; nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, bromothiophene, dibromothiophene, pyrrole, oxazole, thiazole, isooxazole, isothiazole, oxadiazole, tiadiazole, pyrazole, imidazole, triazole, tetrazole, indole, benzofuran, benzothiophene, benzooxazole, benzothiazole, benzooxadiazole, benzothiadiazole, benzopyrazole, benzimidazole, benzotriazole, triazolopyridine, triazolopyrimidine, coumarin.

For the purpose of the present description and the following claims, the term "$C_1$-$C_{30}$ alkoxy groups" means groups comprising an oxygen atom to which a linear or branched, saturated or unsaturated $C_1$-$C_{30}$ alkoxy groups is linked. Specific examples of $C_1$-$C_{30}$ alkoxyl groups are: methoxyl, ethoxyl, n-propoxyl, iso-propoxyl, n-butoxyl, iso-butoxyl, tert-butoxyl, pentoxyl, hexyloxyl, 2-ethylhexyloxyl, 2-hexyldecyloxyl, 2-octyltethradecyloxyl, 2-octyldodecyloxyl, 2-decyltetradecyloxyl, heptyloxyl, octyloxyl, nonyloxyl, decyloxyl, dodecyloxyl.

For the purpose of the present description and the following claims, the term "$C_1$-$C_{30}$ alkylene groups" means alkylene groups having from 1 to 30 linear or branched carbon atoms. Specific examples of $C_1$-$C_{20}$ alkylene groups are: methylene, ethylene, n-propylene, iso-propylene, n-butylene, iso-butylene, tert-butylene, pentylene, ethylhexylene, hexylene, heptylene, octylene, nonylene, decylene, dodecylene.

For the purpose of the present description and the following claims, the term "polyethylene oxyl groups" means groups having oxyethylene units in the molecule. Specific examples of polyethylene oxyl groups are: methyloxy-ethylene oxyl, methyloxy-diethyleneoxyl, 3-oxatetraoxyl, 3,6-dioxaheptyloxyl, 3,6,9-trioxadecyloxyl, 3,6,9,12-tetraoxahexadecyloxyl.

The benzodithiophene conjugated polymer of general formula (I) object of the present disclosure can be obtained by processes known in the art.

For example, the benzodithiophene conjugated polymer of general formula (I) object of the present disclosure can be obtained by a process comprising reacting at least one benzodithiophene derivative of general formula (II):

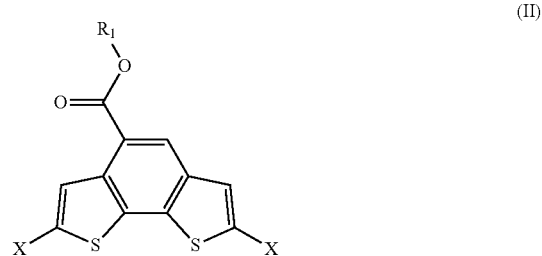

wherein $R_1$ has the same meanings given above and X represents a halogen atom such as, for example, chlorine, fluorine, bromine, iodine, preferably, bromine; or it is selected from the —Sn($R_a$)$_3$ groups wherein $R_a$, mutually identical or different, are selected from linear or branched, preferably $C_2$-$C_{20}$, $C_1$-$C_{30}$ alkyl groups; or from B(O$R_b$)$_3$ groups wherein $R_b$, mutually identical or different, represent a hydrogen atom, or they are selected from linear or branched, preferably $C_2$-$C_{20}$, $C_1$-$C_{30}$ alkyl groups, or the O$R_b$ groups together with the other atoms to which they are linked can form a heterocyclic ring having one of the following formulas:

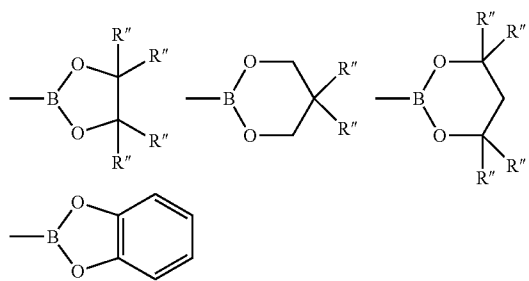

wherein R", mutually identical or different, represent a hydrogen atom, or they are selected from linear or branched, preferably $C_2$-$C_{20}$, $C_1$-$C_{30}$ alkyl groups, with at least one compound of general formula (III):

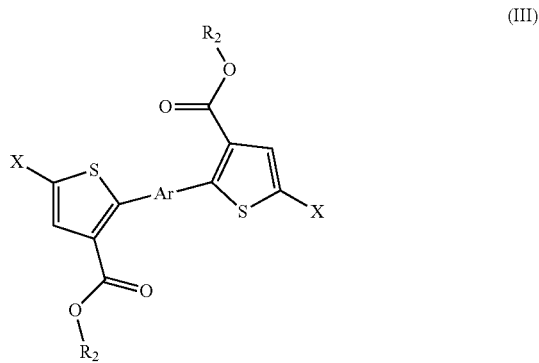

(III)

wherein $R_2$, Ar and X, have the same meanings given above, obtaining a benzodithiophene conjugated polymer of general formula (I).

The aforesaid process can be carried out according to techniques known in the art as described, for example, by Xu J. and others, in the article "Effect of fluorination of the electrochromic performance of benzothiadiazole-based donor-acceptor copolymers", "*Journal of Materials Chemistry*" (2015), Vol. 3, p. 5589-5597: further details regarding the aforesaid process can be found in the following examples.

The benzodithiophene derivative of general formula (II) can be obtained according to processes known in the art as described, for example in the US patent application US 2015/0333265 given above: further details can be found in the following examples.

The compound of general formula (III) can be obtained according to processes known in the art as described, for example, by Li S. and others, in the article "A Wide Band-Gap Polymer with a Deep Highest Occupied Molecular Orbital Level Enables 14.2% Efficiency in Polymer Solar Cells", "*Journal of the American Chemical Society*" (2018), Vol. 140, p. 7159-7167: further details can be found in the following examples.

As said above, said benzodithiophene conjugated polymer of general formula (I), can be advantageously used in the construction of organic devices, in particular photovoltaic devices (or solar devices) such as, for example, photovoltaic cells (or solar cells), photovoltaic modules (or solar modules), either on a rigid support, or on a flexible support.

A further object of the present disclosure is therefore a photovoltaic device (or solar device) such as, for example, a photovoltaic cell (or solar cell), a photovoltaic module (or solar module), either on a rigid support, or on a flexible support, comprising at least one benzodithiophene conjugated polymer of general formula (I).

Furthermore, as said above, said benzodithiophene conjugated polymer of general formula (I), can be advantageously used in the construction of "Organic Thin Film Transistors" (OTFTs), "Organic Field Effect Transistors" (OFETs), or "Organic Light-Emitting Diodes" (OLEDs).

A further object of the present disclosure is therefore an "Organic Thin Film Transistors" (OTFTs), or an "Organic Field Effect Transistors" (OFETs), or an "Organic Light-Emitting Diodes" (OLEDs), comprising at least one benzodithiophene conjugated polymer of general formula (I).

Figure 3:
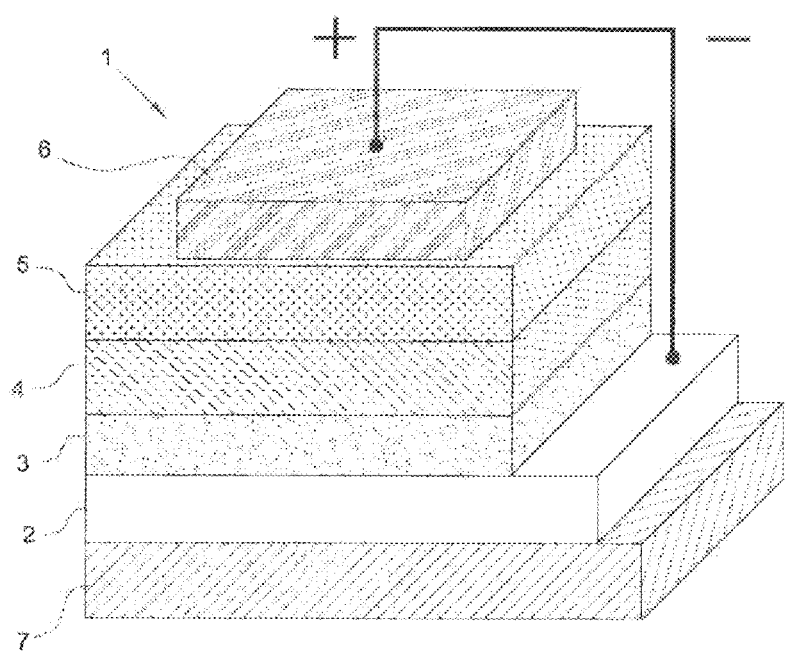
FIG. 3 depicts a cross sectional view of a polymer photovoltaic cell with an inverted structure used in Examples 7-8.

FIG. 3 below shows a cross sectional view of a polymer photovoltaic cell (or solar cell) with inverted structure used in Examples 7-8 given below.

With reference to FIG. 3, the polymeric photovoltaic cell (or solar cell) with inverted structure (1) comprises:
- a transparent glass support (7);
- a cathode (2) of indium-tin oxide (ITO);
- a cathodic buffer layer (3) comprising zinc oxide (ZnO);
- a layer of photoactive material (4) comprising regioregular poly(3-hexylthiophene) (P3HT) or a benzodithiophene conjugated polymer of general formula (I) and methyl ester of the [6,6]-phenyl-$C_{61}$-butyric acid (PC$_{61}$BM);
- an anodic buffer layer (5) comprising molybdenum oxide (MoO$_3$);
- a silver (Ag) anode (6).

In order to better understand the present disclosure and to put it into practice, some illustrative and non-limiting examples thereof are given below.

EXAMPLES

Characterization of the Polymers Obtained
Determination of the Molecular Weight

The molecular weight of the polymers obtained by operating in accordance with the following examples, was determined by "Gel Permeation Chromatography" (GPC) on a WATERS 150C instrument, using HT5432 columns, with trichlorobenzene eluent, at 80° C.

The weight average molecular weight ($M_w$), the number average molecular weight ($M_n$) and the polydispersity index ("PDI"), corresponding to the $M_w/M_n$ ratio, are given.

Determination of the Optical "Band-Gap"

The polymers obtained by operating in accordance with the following examples, were characterized by UV-Vis-NIR spectroscopy to determine the energetic entity of the optical "band-gap" in solution or on thin film according to the following procedure.

In the case that the "optical band-gap" was measured in solution, the polymer was dissolved in toluene, chloroform, chlorobenzene, dichlorobenzene, trichlorobenzene, or other suitable solvent. The solution thus obtained was placed in a quartz cuvette and analysed in transmission by means of a double-beam and double monochromator UV-Vis-NIR spectrophotometer Perkin Elmer λ 950, in the range 200 nm-850 nm, with a 2.0 nm bandwidth, scanning speed of 220 nm/min and 1 nm step, using as a reference an identical quartz cuvette containing only the solvent used as a reference.

In the case that the "optical band-gap" was measured on thin film, the polymer was dissolved in toluene, chloroform, chlorobenzene, dichlorobenzene, trichlorobenzene, or other suitable solvent, obtaining a solution having a concentration equal to about 10 mg/ml, which was deposited by spin-coating on a Suprasil quartz slide. The thin film thus obtained was analysed in transmission by means of a dual-beam and double monochromator UV-Vis-NIR spectrophotometer Perkin Elmer λ 950, in the range 200 nm-850 nm, with a 2.0 nm bandwidth, scanning speed of 220 nm/min and 1 nm step, using an identical Suprasil quartz slide as such, as a reference.

The optical "band-gap" was estimated from the spectra in transmission by measuring the absorption edge corresponding to the transition from the valence band (VB) to the conduction band (CB). The intersection with the abscissa axis of the straight line tangent to the absorption band at the inflection point was used for the determination of the edge.

The inflection point ($\lambda_F$, $y_F$) was determined on the basis of the coordinates of the minimum of the spectrum in the first derivative, indicated with $\lambda'_{min}$ and $y'_{min}$.

The equation of the straight line tangent to the UV-Vis spectrum at the inflection point ($\lambda_F$, $y_F$) is as follows:

$$y = y'_{min}\lambda + y_F - y'_{min}\lambda'_{min}.$$

Finally, from the condition of intersection with the abscissa axis $\psi=0$, it was obtained:

$$\lambda_{EDGE} = (y'_{min}\lambda'_{min} - y_F)/y'_{min}.$$

Therefore, by measuring the coordinates of the minimum of the first derivative spectrum and the corresponding absorbance value $y_F$ from the UV-Vis spectrum, $\lambda_{EDGE}$ was obtained directly by substitution.

The corresponding energy is:

$$E_{EDGE} = h\nu_{EDGE} = hc/\lambda_{EDGE}$$

wherein:
h=6.626 10-34 J s;
c=2.998 108 m s$^{-1}$;
that is:

$$E_{EDGE} = 1.988 \; 10\text{-}16 \; J/\lambda_{EDGE} \; (nm).$$

Lastly, remembering that 1 J=6.24 1018 eV, we have:

$$E_{EDGE} = 1240 \; eV/\lambda_{EDGE} \; (nm).$$

Determination of HOMO and LUMO

The determination of the HOMO and LUMO values of the polymers obtained by operating in accordance with the following examples, was carried out using the cyclic voltammetry (CV) technique. This technique makes it possible to measure the values of the potentials of formation of the radical cation and radical anion of the sample under examination. These values, inserted in a special equation, allow the HOMO and LUMO values of the polymer in question to be obtained. The difference between HOMO and LUMO makes the value of the electrochemical "band-gap".

The values of the electrochemical "band-gap" are generally higher than the values of the optical "band-gap" since during the execution of the cyclic voltammetry (CV), the neutral compound is charged and undergoes a conformational reorganization, with an increase in the energy gap, while optical measurement does not lead to the formation of charged species.

The cyclic voltammetry (CV) measurements were carried out with an Autolab PGSTAT12 potentiostat (with GPES Ecochemie software) in a three-electrode cell. In the measurements carried out, an Ag/AgCl electrode was used as the reference electrode, a platinum wire as the counter electrode and a glassy graphite electrode as the working electrode. The sample to be analysed was dissolved in a suitable solvent and subsequently deposited, with a calibrated capillary, on the working electrode, so as to form a film. The electrodes were immersed in a 0.1 M electrolytic solution of 95% tetrabutylammonium tetrafluroborate in acetonitrile. The sample was subsequently subjected to a cyclic potential in the shape of a triangular wave. At the same time, as a function of the applied potential difference, the current, which signals the occurrence of oxidation or reduction reactions of the present species, was monitored.

The oxidation process corresponds to the removal of an electron from HOMO, while the reduction cycle corresponds to the introduction of an electron into LUMO. The potentials of formation of radical cation and radical anion were derived from the value of the peak "onset" ($E_{onset}$), which is caused by molecules and/or chain segments with HOMO-LUMO levels closer to the edges of the bands. The electrochemical potentials to those related to the electronic levels can be correlated if both refer to the vacuum. For this purpose, the potential of ferrocene in vacuum, known in the literature and equal to −4.8 eV, was taken as a reference. The inter-solvent redox pair ferrocene/ferrocinium (Fc/Fc$^+$) was selected because it has an oxide-reduction potential independent of the working solvent.

The general formula for calculating the energies of the HOMO-LUMO levels is therefore given by the following equation:

$$E(eV) = -4.8 + [E_{1/2 \, Ag/AgCl}(Fc/Fc^+) - E_{onset \, Ag/AgCl} \, (polymer)]$$

wherein:
E=HOMO or LUMO according to the entered $E_{onset}$ value;
$E_{1/2 \, Ag/AgCl}$=half-wave potential of the peak corresponding to the redox pair ferrocene/ferrocinium measured under the same analysis conditions as the sample and with the same trio of electrodes used for the sample;
$E_{onset \, Ag/AgCl}$="onset" potential measured for the polymer in the anodic area when calculating HOMO and in the cathodic area when calculating LUMO.

Example 1

Preparation of 2-octyldodecyl-benzo[2,1-b; 3,4-b'] dithiophene-4-carboxylate of formula (C)

In a 250 ml flask, equipped with coolant and magnetic stirring, the following were charged, under argon flow, in the order: 3-thiopheneacetic acid (Aldrich) (0.711 g; 5 mmoles), palladium(II)acetate [Pd(OAc)$_2$] (Aldrich) (0.023 g; 0.1 mmol), triphenylphosphine [PPh$_3$] (Aldrich) (0.052 g; 0.2 mmol), potassium carbonate [K$_2$CO$_3$] (Aldrich) (1.382 g; 10 mmol), anhydrous N,N-dimethylformamide (DMF) (Aldrich) (30 ml) and 2-bromothiophene-3-carbaldehyde (Aldrich) (0.955 g; 5 mmoles): the reaction mixture was heated to 110° C. and kept at said temperature, under stirring, for 12 hours. Subsequently, the reaction mixture was cooled to room temperature (25° C.) and 9-(bromomethyl)nonadecane (Sunatech) (3.614 g; 10 mmol) was added: the reaction mixture was left, under stirring, at room temperature (25° C.), for 4 hours. Subsequently, the reaction mixture was placed in a 500 ml separating funnel, diluted with a 0.1 M ammonium chloride solution (NH$_4$Cl) (Aldrich) (3×100 ml) and extracted with ethyl acetate (Aldrich) (3×100 ml), obtaining an aqueous phase and an organic phase. The entire organic phase (obtained by combining the organic phases deriving from the three extractions) was washed to neutral with water (3×50 ml) and subsequently anidrified on sodium sulphate (Aldrich) and evaporated. The residue obtained was purified by elution on a chromatographic column of silica gel [(eluent: n-heptane/ethyl acetate, 9/1, v/v) (Carlo Erba)], obtaining 2.342 g of 2-octyldodecyl-benzo[2,1-b;3,4-b']dithiophene-4-carboxylate of formula (C) as straw yellow oil (yield 91%).

Example 2

Preparation of 2-octyldodecyl-2,7-bis (tributylstannyl)-benzo[2,1-b;3,4-b']dithiophene-4-carboxylate of formula (IIa)

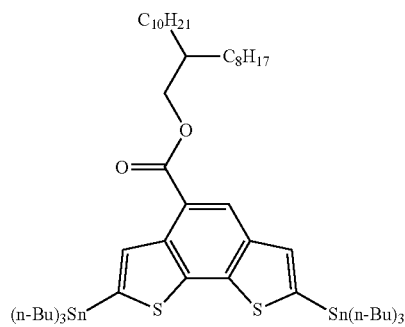

(IIa)

In a 250 ml flask, equipped with magnetic stirring, the following were charged, under argon flow, in the order: 2-octyldodecyl-benzo[2,1-b;3,4-b']dithiophene-4-carboxylate (1.029 g; 2 mmoles) obtained as described in Example 1 and anhydrous tetrahydrofuran (THF) (Aldrich) (60 ml): the reaction mixture was cooled to −78° C. and kept at said temperature, under stirring, for about 10 minutes. Subsequently, by dripping, 4.4 ml of a lithium di-iso-propylamine solution (LDA) (Aldrich) were added in a mixture tetrahydrofuran (THF) (Aldrich)/hexane (Aldrich) (1/1, v/v) 1.0 M (0.471 g; 4.4 mmoles): the reaction mixture was kept at −78° C., under stirring, for 3 hours. Subsequently, 0.678 ml of tributyltin chloride (Aldrich) (1.627 g; 5 mmoles) were added by dripping: the reaction mixture was kept at −78° C., under stirring, for 30 minutes, then brought to room temperature (25° C.) and kept at said temperature, under stirring, for 16 hours. Subsequently, the reaction mixture was placed in a 500 ml separating funnel, diluted with a 0.1 M sodium bicarbonate solution (Aldrich) (200 ml) and extracted with diethyl ether (Aldrich) (3×100 ml), obtaining an acid aqueous phase and an organic phase. The entire organic phase (obtained by combining the organic phases deriving from the three extractions) was washed to neutral with water (3×50 ml) and subsequently anidrified on sodium sulphate (Aldrich) and evaporated. The obtained residue was purified by elution on a chromatographic column of silica (Aldrich) pre-treated with a mixture of n-heptane (Aldrich)/triethylamine (TEA) (Aldrich) (9/1, v/v), [(eluent: n-heptane) (Carlo Erba)], obtaining 3.716 g of 2-octyldodecyl-2,7-bis (tributylstannyl)benzo[2,1-b;3,4-b']dithiophene-4-carboxylate of formula (IIa) as straw yellow oil (yield 85%).

Example 3

Preparation of octyl-2-bromothiophene-3-carboxylate of formula (A)

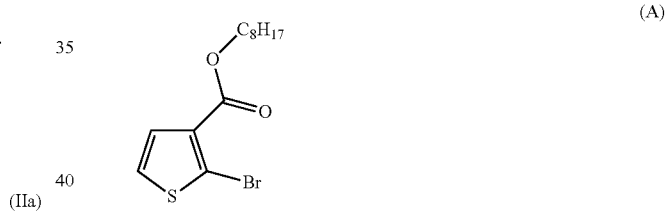

(A)

In a 100 ml flask, equipped with coolant and magnetic stirring, the following was charged under argon flow, in the order: 2-bromo-3-thiophenecarboxylic acid (Aldrich) (2.07 g; 10 mmoles), N,N'-dicyclohexylcarbodiimide (DCC) (Aldrich) (1.032 g; 5 mmoles), 4-(dimethylamino)pyridine (DMAP) (Aldrich) (0.305 g; 2 mmoles), anhydrous dichloromethane (DCM) (Aldrich) (20 ml) and, after 5 minutes, 1-octanol (Aldrich) (1.302 g; 10 mmol) (Aldrich) was added by dripping: the reaction mixture was kept under stirring at room temperature (25° C.), for 24 hours. Subsequently, the reaction mixture was placed in a 500 ml separating funnel, diluted with distilled water (150 ml) and extracted with dichloromethane (DCM) (Aldrich) (3×100 ml), obtaining an aqueous phase and an organic phase. The entire organic phase (obtained by combining the organic phases deriving from the three extractions) was anidrified on sodium sulphate (Aldrich) and evaporated. The residue obtained was purified by elution on a chromatographic column of silica gel [(eluent: n-heptane/ethyl acetate, 9/1, (v/v) (Carlo Erba)], obtaining 2.554 g of octyl-2-bromothiophene-3-carboxylate of formula (A) as a colourless oil (yield 80%).

Example 4

Preparation of dioctyl-2,2':5',2"-tert-thiophene-3,3"-dicarboxylate of formula (B)

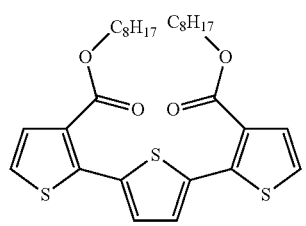

(B)

In a 100 ml flask, equipped with coolant and magnetic stirring, the following was charged, under argon flow, in the order: octyl-2-bromothiophene-3-carboxylate obtained as described in Example 3 (1.596 g; 5 mmoles), anhydrous toluene (Aldrich) (30 ml), 2,5-bis (trimethylstannyl)thiophene (Aldrich) (0.819 g; 2 mmoles) (Aldrich), tris(dibenzylideneacetone)dipalladium(0) [Pd$_2$(dba)$_3$] (Aldrich) (0.055 g; 0.06 mmol) and tri(o-tolyl)phosphine [P(o-tol)$_3$] (Aldrich) (0.061 g; 0.2 mmol): the reaction mixture was heated to 115° C. and kept at said temperature, under stirring, for 5 hours. Subsequently, the reaction mixture was concentrated by rotovapor and the residue obtained was purified by elution on a chromatographic column of silica gel [(eluent: n-heptan/ethyl acetate, 9/1, v/v) (Carlo Erba)], obtaining 1.054 g of dioctyl-2,2':5',2"-tert-thiophene-3,3"-dicarboxylate of formula (B) as straw yellow oil (yield 94%).

Example 5

Preparation of dioctyl-5,5"-dibromo-2,2':5',2"-tert-thiophene-3,3"-Dicarboxylate of Formula (IIIa)

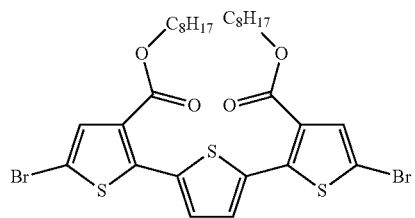

(IIIa)

In a 100 ml flask, equipped with magnetic stirring, the following was charged, under argon flow, in the order: dioctyl-2,2':5',2"-tert-thiophene-3,3"-dicarboxylate of formula (B) obtained as described in Example 4 (1.009 g; 1.8 mmoles), anhydrous chloroform (Aldrich) (20 ml) and N-bromosuccinimide (Aldrich) (0.365 g; 2.05 mmoles): the reaction mixture was kept, under stirring, at room temperature (25° C.), for 20 hours. Subsequently, the reaction mixture was placed in a 500 ml separating funnel, diluted with distilled water (150 ml) and extracted with dichloromethane (DCM) (Aldrich) (3×100 ml), obtaining an aqueous phase and an organic phase. The entire organic phase (obtained by combining the organic phases deriving from the three extractions) was anidrified on sodium sulphate (Aldrich) and evaporated. The residue obtained was purified by elution on a chromatographic column of silica gel [(eluent: n-heptane/dichloromethane, 9/1, v/v (Carlo Erba)], obtaining 1.164 g of dioctyl-5,5"-dibromo-2,2':5',2"-tert-thiophene-3,3"-dicarboxylate of formula (IIIa) as yellow-orange oil (90% yield).

Example 6

Preparation of the Benzodithiophene Conjugated Polymer of Formula (Ia)

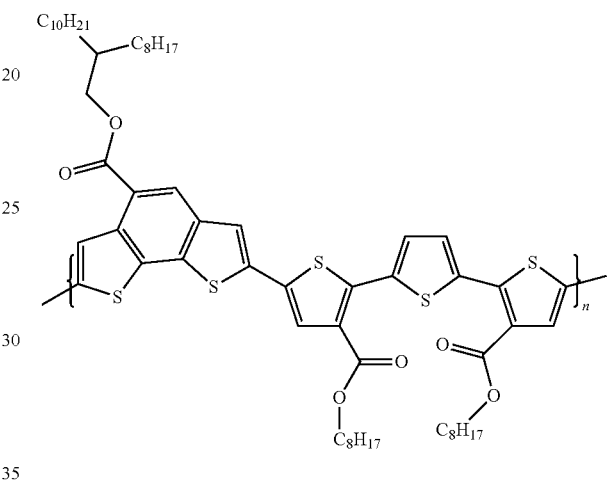

(Ia)

In a 100 ml flask, equipped with magnetic stirring, thermometer and coolant, the following was charged, under argon flow, in the order: dioctyl-5,5"-dibromo-2,2':5',2"-tert-thiophene-3,3"-dicarboxylate of formula (IIIa) obtained as described in Example 5 (0.719 g; 1.001 mmoles), toluene (Aldrich) (80 ml), 2-octyldodecyl-2,7-bis(tributylstannyl)benzo[2,1-b;3,4-b']dithiophene-4-carboxylate of formula (IIa) obtained as described in Example 2 (1.2 g; 1.097 mmoles), tris(dibenzylideneacetone)dipalladium (0) [Pd$_2$(dba)$_3$] (Aldrich) (0.018 g; 0.02 mmol) and tris(o-tolyl)phosphine [P(o-tol)$_3$] (Aldrich) (0.031 g; 0.1 mmoles): the reaction mixture was heated to 100° C. and kept at said temperature, under stirring, for 24 hours. The colour of the reaction mixture turned dark red after 3 hours and turned dark brick red at the end of the reaction (i.e. after 24 hours). Subsequently, after cooling to room temperature (25° C.), the reaction mixture obtained was placed in methanol (Aldrich) (300 ml) and the precipitate obtained was subjected to sequential extraction in a Soxhlet apparatus with methanol (Aldrich), acetone (Aldrich), n-heptane (Aldrich) and, finally, chloroform (Aldrich). The residue remained inside the extractor was dissolved in chlorobenzene (Aldrich) (50 ml) at 80° C. The hot solution was precipitated in methanol (Aldrich) (300 ml). The obtained precipitate was collected and dried under vacuum at 50° C. for 16 hours, obtaining 1.014 g of a dark violet solid product (95% yield), corresponding to the benzodithiophene conjugated polymer of formula (Ia).

Said solid product was subjected to the above characterizations obtaining the following data:

(M$_w$)=85617 Dalton;
(PDI)=2.2384.
($\lambda_{EDGE}$ sol.)=610 nm;
($\lambda_{EDGE}$ film)=620 nm;
E$_{g.opt.sol.}$=2.01 eV;
E$_{g.opt.film}$=1.99 eV;
(HOMO)=−5.42 eV

Example 7 (Comparative)

Solar Cell Comprising Regioregular Poly-3-Hexylthiophene (P3HT)

For this purpose, a polymeric solar cell with inverted structure was used, schematically represented in FIG. 3.

For this purpose, a polymer-based device was prepared on an ITO (indium-tin oxide) coated glass substrate (Kintec Company—Hong Kong), previously subjected to a cleaning procedure consisting of a manual cleaning, rubbing with a lint-free cloth soaked in a detergent diluted with tap water. The substrate was then rinsed with tap water. Subsequently, the substrate was thoroughly cleaned using the following methods in sequence: ultrasonic baths in (i) distilled water plus detergent (followed by manual drying with a lint-free cloth); (ii) distilled water [followed by manual drying with a lint-free cloth]; (iii) acetone (Aldrich) and (iv) iso-propanol (Aldrich) in sequence. In particular, the substrate was placed in a beaker containing the solvent, placed in an ultrasonic bath, kept at 40° C., for a treatment of 10 minutes. After treatments (iii) and (iv), the substrate was dried with a compressed nitrogen flow.

Subsequently, the glass/ITO was further cleaned in an air plasma device (Tucano type—Gambetti), immediately before proceeding to the next step.

The substrate thus treated was ready for the deposition of the cathodic buffer layer. For this purpose, the zinc oxide (ZnO) buffer layer was obtained starting from a 0.162 M solution of the complex [Zn$^{2+}$]-ethanolamine (Aldrich) in butanol (Aldrich). The solution was deposited by rotation on the substrate operating at a rotation speed equal to 600 rpm (acceleration equal to 300 rpm/s), for 2 minutes and 30 seconds, and subsequently at a rotation speed equal to 1500 rpm, for 5 seconds. Immediately after deposition of the cathodic buffer layer, zinc oxide formation was obtained by thermally treating the device at 140° C. for 5 minutes on a hot plate in ambient air. The cathodic buffer layer thus obtained had a thickness equal to 30 nm and was partially removed from the surface with 0.1 M acetic acid (Aldrich), leaving the layer only on the desired surface.

The active layer was deposited, comprising regioregular poly-3-hexylthiophene (P3HT) (Plexcore OS) and methyl ester of the [6,6]-phenyl-C$_{61}$-butyric acid (PCBM) (Aldrich), on the cathodic buffer layer thus obtained by "spin coating" of a 1/0.8 (v/v) solution in o-dichlorobenzene (Aldrich) with a P3HT concentration equal to 10 mg/ml which had been kept under stirring overnight, operating at a rotation speed of 300 rpm (acceleration equal to 255 rpm/s), for 90 seconds. The thickness of the active layer was found to be 250 nm.

On the active layer thus obtained, the anodic buffer layer was deposited, which was obtained by depositing molybdenum oxide (MoO$_3$) (Aldrich) through a thermal process: the thickness of the anodic buffer layer was equal to 10 nm. A silver (Ag) anode, having a thickness equal to 100 nm, was deposited on the anodic buffer layer by vacuum evaporation, appropriately masking the area of the device in order to obtain an active area equal to 25 mm$^2$.

The depositions of the anodic buffer layer and of the anode were carried out in a standard evaporation chamber under vacuum containing the substrate and two evaporation vessels equipped with a heating resistance containing 10 mg of molybdenum oxide (MoO$_3$) in powder and 10 (Ag) silver shots (diameter 1 mm-3 mm) (Aldrich), respectively. The evaporation process was carried out under vacuum, at a pressure of about 1×10$^{-6}$ bar. The molybdenum oxide (MoO$_3$) and silver (Ag), after evaporation, are condensed in the unmasked parts of the device.

The thicknesses were measured with a Dektak 150 (Veeco Instruments Inc.) profilometer.

The electrical characterization of the device obtained was carried out in a controlled atmosphere (nitrogen) in a "glove box", at room temperature (25° C.). The current-voltage curves (I-V) were acquired with a Keithley® 2600A multimeter connected to a personal computer for data collection. The photocurrent was measured by exposing the device to the light of an ABET SUN® 2000-4 solar simulator, capable of providing 1.5G AM radiation with an intensity equal to 100 mW/cm$^2$ (1 sun), measured with a Ophir Nova® II powermeter connected to a 3A-P thermal sensor. The device, in particular, is masked before said electrical characterization, so as to obtain an effective active area equal to 16 mm$^2$: Table 1 shows the four characteristic parameters as average values.

Example 8 (Disclosure)

Solar Cell Disclosure Comprising the Benzodithiophene Conjugated Polymer of

Formula (Ia) A polymer-based device was prepared on an ITO (indium-tin oxide) coated glass substrate (Kintec Company—Hong Kong), previously subjected to a cleaning procedure operating as described in Example 7.

The deposition of the cathodic buffer layer and the deposition of the anodic buffer layer were carried out as described in Example 7; the composition of said cathodic buffer layer and the composition of said anodic buffer layer are the same as the ones in Example 7; the thickness of said cathodic buffer layer and the thickness of said anodic buffer layer are the same as the ones in Example 7.

The active layer, comprising the benzodithiophene conjugated polymer of formula (Ia) obtained as described in Example 6 and methyl ester of the [6,6]-phenyl-C$_{61}$-butyric acid (PCBM) (Aldrich), was deposited on the cathodic buffer layer thus obtained by spin coating of a 1/1.5 (v/v) solution in o-dichlorobenzene (Aldrich) with a conjugated polymer concentration of formula (Ia) equal to 18 mg/ml which had been kept under stirring overnight, operating at a rotation speed equal to 5000 rpm (acceleration equal to 2500 rpm/s), for 30 seconds. The thickness of the active layer was found to be 60 nm.

The deposition of the silver (Ag) anode was carried out as described in Example 7: the thickness of said silver anode (Ag) is the same as the one given in Example 7.

The thicknesses were measured with a Dektak 150 (Veeco Instruments Inc.) profilometer.

The electrical characterization of the obtained device was carried out as described in Example 7: Table 1 shows the four characteristic parameters as average values.

FIG. 1 shows the current-voltage curve (I-V) obtained [the abscissa shows the voltage in volts (V); the ordinate shows the short circuit current density (Jsc) in milliamps/cm$^2$ (mA/cm$^2$)].

Figure 2:
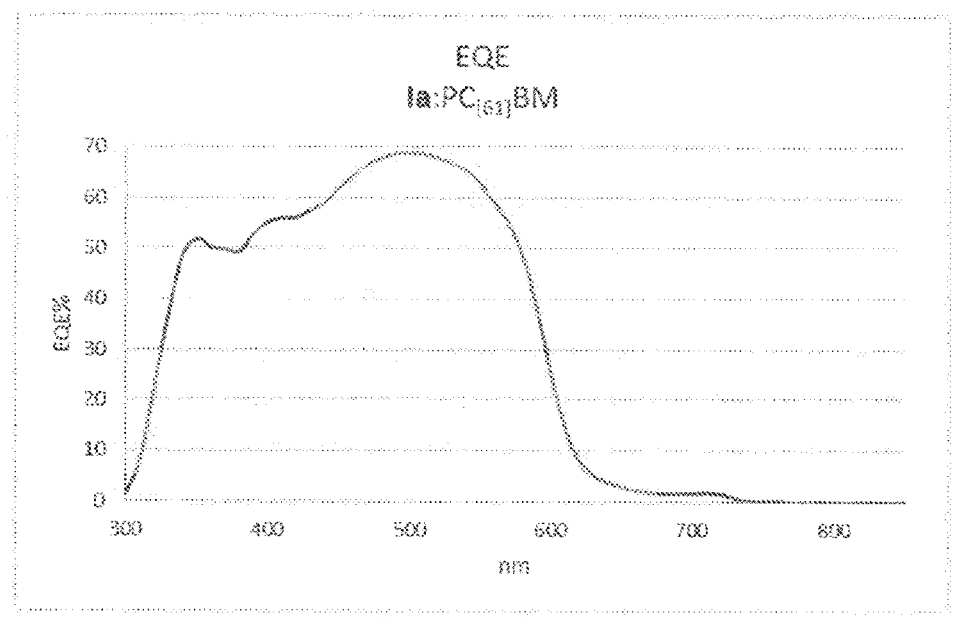
FIG. 2 is a plot of the curve relating to the External Quantum Efficiency (EQE) recorded under a monochromatic light wherein the abscissa depicts the wavelength in nanometers (nm) and the ordinate depicts the External Quantum Efficiency (EQE) in percent (%).

FIG. 2 shows the curve relating to the External Quantum Efficiency (EQE) which was recorded under a monochromatic light (obtained using the TMc300F-U (I/C)—"Triple grating monochromator" and a double source with a Xenon lamp and a halogen lamp with quartz) in an instrument from Bentham Instruments Ltd [the abscissa shows the wavelength in nanometers (nm); the ordinate shows the External Quantum Efficiency (EQE) in percent (%)].

TABLE 1

| EXAMPLE | FF[1] | $V_{OC}$[2] (V) | $J_{SC}$[3] (mA/cm$^2$) | $PCE_{av}$[4] (%) |
|---|---|---|---|---|
| 7 (comparative) | 0.57 | 0.56 | 10.10 | 3.30 |
| 8 (disclosure) | 0.65 | 0.92 | 8.25 | 4.97 |

[1]FF (Fill Factor) is calculated according to the following equation:

$$\frac{V_{MPP} \cdot J_{MPP}}{V_{OC} \cdot J_{SC}}$$

wherein $V_{MPP}$ and $J_{MPP}$ are voltage and current density, respectively corresponding to the point of maximum power, $V_{OC}$ is the open circuit voltage and $J_{SC}$ is the short circuit current density;
[2]$V_{OC}$ is the open circuit voltage;
[3]$J_{SC}$ is the short circuit current density;
[4]$PCE_{av}$ is the device efficiency calculated according to the following equation:

$$\frac{V_{OC} \cdot J_{SC} \cdot FF}{P_{in}}$$

wherein $V_{OC}$, $J_{SC}$ and FF have the same meanings given above and $P_{in}$ is the intensity of the incident light on the device.

The invention claimed is:
1. A benzodithiophene conjugated polymer of general formula (I):

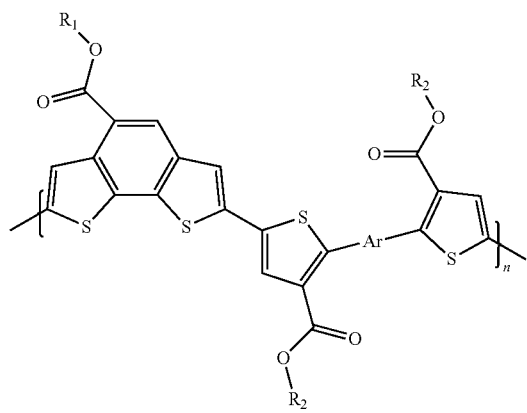

(I)

wherein:
$R_1$ and $R_2$, mutually identical or different, are selected from linear or branched, saturated or unsaturated, $C_1$-$C_{30}$ alkyl groups; cycloalkyl groups optionally substituted; aryl groups optionally substituted; heteroaryl groups optionally substituted; linear or branched, $C_1$-$C_{30}$ alkoxy groups; thiol groups -S-$R_3$ wherein the $R_3$ is selected from linear or branched, saturated or unsaturated, $C_1$-$C_{30}$ alkyl groups; polyethyleneoxy groups $R_4$ -O-[$CH_2$—$CH_2$-O]$_m$-, wherein $R_4$ is selected from linear or branched, saturated or unsaturated, $C_1$-$C_{30}$ alkyl groups, and m is an integer ranging from 1 to 4; -$R_5$—$OR_6$ groups, wherein the $R_5$ is selected from linear or branched, $C_1$-$C_{30}$ alkylene groups, and the $R_6$ represents a hydrogen atom or is selected from linear or branched, saturated or unsaturated, $C_1$-$C_{30}$ alkyl groups; —$COR_7$ groups, wherein the $R_7$ is selected from linear or branched, saturated or unsaturated, $C_1$-$C_{30}$ alkyl groups; —$COOR_8$ groups, wherein the $R_8$ is selected from linear or branched, saturated or unsaturated, $C_1$-$C_{30}$ alkyl groups; polyethyleneoxy groups $R_9$-[—$OCH_2$—$CH_2$—]$_p$, wherein the $R_9$ is selected from linear or branched, saturated or unsaturated, $C_1$-$C_{30}$ alkyl groups, and p is an integer ranging from 1 to 4; $R_{10}$—T groups, wherein the $R_{10}$ is selected from linear or branched, saturated or unsaturated, $C_1$-$C_{30}$ alkyl groups and the T represents a polyalcohol group —$OCH_2$—CHOH—$CH_2OH$, an amino group -N($CH_3$)$_2$, a carboxylic group —$CO_2H$, a —CHO group, or a cyano group (—CN);

wherein Ar represents an electron-acceptor group or an electron-donor group;

wherein n is an integer ranging from 10 to 500.

2. The benzodithiophene conjugated polymer of general formula (I) according to claim 1, wherein in said general formula (I), the Ar is selected from the group consisting of

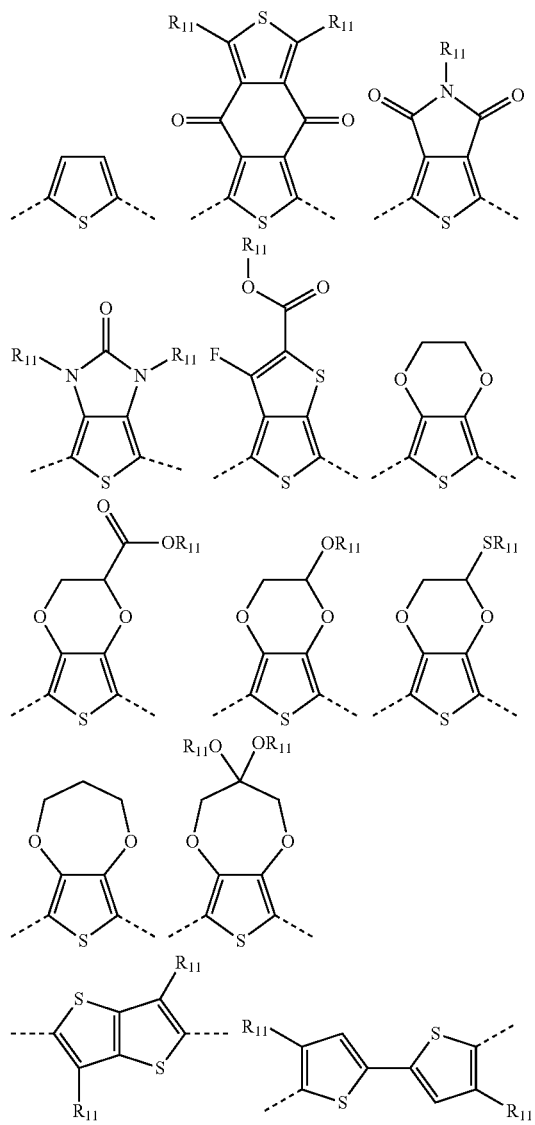

-continued

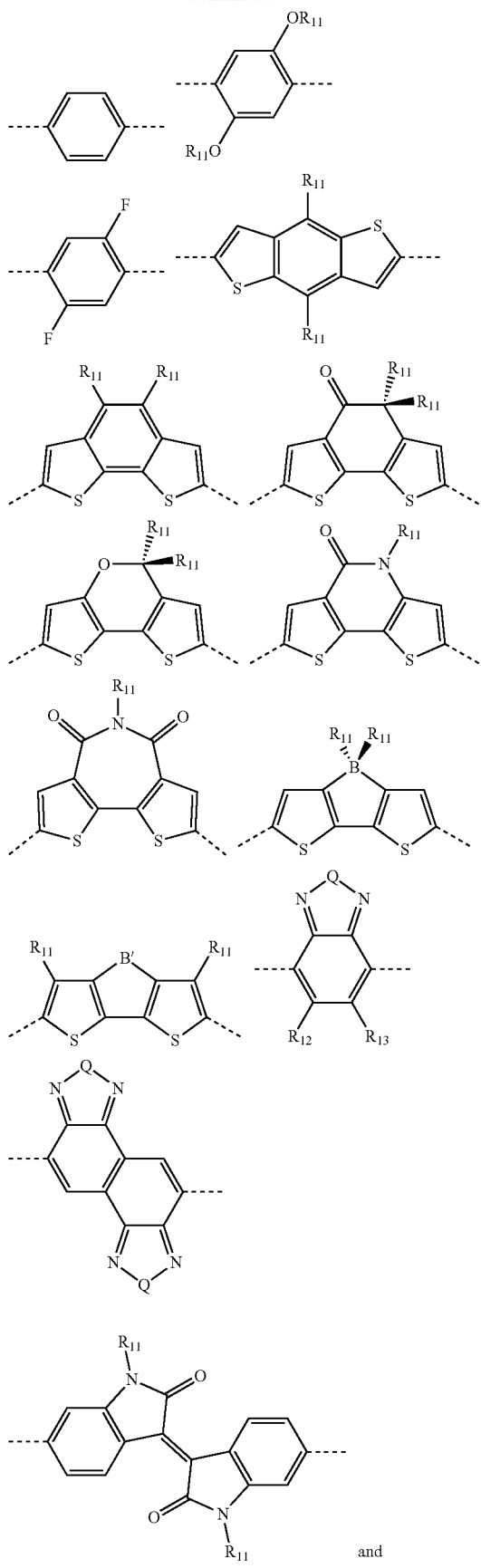

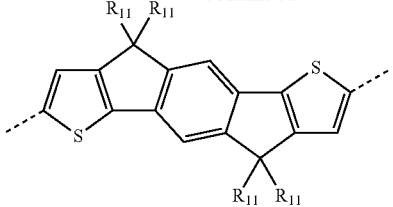

and

-continued wherein:
B represents a sulfur atom, an oxygen atom, a selenium atom, or a N-$R_{14}$ group, wherein the $R_{14}$ represents a hydrogen atom or is selected from linear or branched, saturated or unsaturated, $C_1$-$C_{30}$ alkyl groups;

B' represents a carbon atom, a silicon atom, or a germanium atom;

Q represents a nitrogen atom, a sulfur atom, an oxygen atom, a selenium atom, or a C-$R_{14}$ group, wherein the $R_{14}$ has the same meanings given above;

$R_{11}$, mutually identical or different, are selected from linear or branched, saturated or unsaturated, $C_1$-$C_{30}$ alkyl groups; cycloalkyl groups optionally substituted; aryl groups optionally substituted; heteroaryl groups optionally substituted; linear or branched, saturated or unsaturated, $C_1$-$C_{30}$ alkoxy groups; polyethyleneoxy groups $R_{15}$—[—$OCH_2$—$CH_2$—$]_q$—, wherein the $R_{15}$ is selected from linear or branched, saturated or unsaturated, $C_1$-$C_{30}$ alkyl groups, and q is an integer ranging from 1 to 4; -$R_{16}$—$OR_{17}$ groups, wherein the $R_{16}$ is selected from linear or branched, saturated or unsaturated, $C_1$-$C_{30}$ alkylene groups, and the $R_{17}$ represents a hydrogen atom or is selected from linear or branched, saturated or unsaturated $C_1$-$C_{30}$ alkyl groups; —$COR_{17}$ groups, wherein the $R_{17}$ has the same meanings given above; —$COOR_{17}$ groups, wherein $R_{17}$ has the same meanings given above; or represent a group —CHO or a cyano group (—CN);

$R_{12}$ and $R_{13}$, mutually identical or different, represent a hydrogen atom, a fluorine atom, or are selected from linear or branched, saturated or unsaturated, $C_1$-$C_{30}$ alkyl groups; cycloalkyl groups optionally substituted; aryl groups optionally substituted;

from linear or branched, $C_1$-$C_{30}$ alkoxy groups; polyethyleneoxy groups $R_{15}$—[—$OCH_2$—$CH_2$—$]_q$—, wherein the $R_{15}$ has the same meanings given above and the q is an integer ranging from 1 to 4; -$R_{16}$—$OR_{17}$ groups, wherein $R_{16}$ and $R_{17}$ have the same meanings given above; —$COR_{17}$ groups, wherein the $R_{17}$ has the same meanings above; —$COOR_{17}$ groups, wherein the $R_{17}$ has the same meanings above; or a group —CHO, or a cyano group (—CN);

$R_{12}$ and $R_{13}$, may be optionally linked to each other so as to form, together with the carbon atoms to which they are bonded, a saturated, unsaturated, or aromatic, cycle or a polycyclic system containing from 3 to 14 carbon atoms, optionally containing one or more heteroatoms selected from the group consisting of oxygen, sulfur, nitrogen, silicon, phosphorus, and selenium.

3. The benzodithiophene conjugated polymer of general formula (I) according to claim 1, wherein in said general formula (I):

$R_1$ is selected from linear or branched, $C_1$-$C_{30}$ alkyl groups;

R₂, mutually identical or different, are selected from linear or branched, saturated or unsaturated, $C_1$-$C_{30}$ alkyl groups;

Ar represents an electron-donor group;

n is an integer ranging from 20 to 300.

4. A photovoltaic device, comprising at least one benzodithiophene conjugated polymer of general formula (I) according to claim 1.

5. An organic thin film transistor, comprising at least one benzodithiophene conjugated polymer of general formula (I) according to claim 1.

6. An organic field effect transistor, comprising at least one benzodithiophene conjugated polymer of general formula (I) according to claim 1.

7. An organic light emitting diode, comprising at least one benzodithiophene conjugated polymer of general formula (I) according to claim 1.

8. The benzodithiophene conjugated polymer of general formula (I) according to claim 1, wherein the $C_{1-30}$ alkyl groups are $C_2$-$C_{20}$ alky groups, and wherein the $C_{1-30}$ alkylene groups are $C_2$-$C_{20}$ alkylene groups, wherein n is an integer ranging from 20 to 300.

9. The benzodithiophene conjugated polymer of general formula (I) according to claim 2, wherein the $C_{1-30}$ alkyl groups are $C_2$-$C_{20}$ alky groups.

10. The benzodithiophene conjugated polymer of general formula (I) according to claim 2, wherein the aromatic, cycle or a polycyclic system contains from 4 to 6 carbon atoms.

11. The benzodithiophene conjugated polymer of general formula (I) according to claim 3, wherein the $C_{1-30}$ alkyl groups are $C_2$-$C_{20}$ alky groups.

12. The benzodithiophene conjugated polymer of general formula (I) according to claim 3, wherein $R_1$ is 2-octyl dodecyl group.

13. The benzodithiophene conjugated polymer of general formula (I) according to claim 3, wherein $R_2$ is an n-octyl group.

14. The photovoltaic device of claim 4, comprising a photovoltaic cell.

15. The photovoltaic device of claim 4, comprising a photovoltaic module.

16. The photovoltaic device of claim 14, wherein the photovoltaic cell is on a rigid support.

17. The photovoltaic device of claim 14, wherein the photovoltaic cell is on a flexible support.

18. The photovoltaic device of claim 15, wherein the photovoltaic module is on a rigid support.

19. The photovoltaic device of claim 15, wherein the photovoltaic module is on a flexible support.

\* \* \* \* \*